United States Patent
Wilhelm et al.

(10) Patent No.: US 8,067,622 B2
(45) Date of Patent: Nov. 29, 2011

(54) METHOD FOR PRODUCING NARINGENIN DERIVATIVES FROM XANTHOHUMOL

(75) Inventors: Heike Wilhelm, Halle (DE); Ludger A. Wessjohann, Halle (DE); Martin Biendl, Elsendorf (DE)

(73) Assignee: Hopsteiner-Hallertauer Hopfenveredelungsgesellschaft M.B.H., Mainburg (DE)

( * ) Notice: Subject to any disclaimer, the term of this patent is extended or adjusted under 35 U.S.C. 154(b) by 878 days.

(21) Appl. No.: 11/908,427

(22) PCT Filed: Feb. 7, 2006

(86) PCT No.: PCT/EP2006/001061
§ 371 (c)(1),
(2), (4) Date: Apr. 1, 2008

(87) PCT Pub. No.: WO2006/099914
PCT Pub. Date: Sep. 28, 2006

(65) Prior Publication Data
US 2009/0227806 A1    Sep. 10, 2009

(30) Foreign Application Priority Data
Mar. 22, 2005 (DE) .......................... 10 2005 013 258

(51) Int. Cl.
*C07D 311/00* (2006.01)

(52) U.S. Cl. ...................................................... 549/403
(58) Field of Classification Search ................... 549/403
See application file for complete search history.

(56) References Cited

OTHER PUBLICATIONS

International Search Report and Written Opinion, Application No. PCT/EP2006/001061, dated Apr. 25, 2006.
Hansel et al.; Desmethylxanthohumol: Isolierung aus Hopfen and Cyclisierung zu Flavanonen; Arch. Pharm. (Weinhelm) 321. 37-40 (1988).
Wang et al.; "A Facile Synthetic Approach to Prenylated Flavanones: First Total Synthesis of (±) Bonannione A and (±)-Sopharaflavanone A"; J. Nat. Prod., 2001, 64, 196-199.

*Primary Examiner* — Andrew D Kosar
*Assistant Examiner* — Raymond Covington
(74) *Attorney, Agent, or Firm* — Renner, Otto, Boisselle & Sklar, LLP

(57) ABSTRACT

The present invention relates to an efficient method for producing naringenin derivatives from xanthohumol or derivatives thereof. In particular, the method according to the present invention provides the production of isoxanthohumol, for example also in enantiomer-enriched form, from xanthohumol and subsequent demethylation of isoxanthohumol according to specific procedures obtaining corresponding naringenin derivatives, such as, in particular, 8-prenylnaringenin.

10 Claims, No Drawings

METHOD FOR PRODUCING NARINGENIN DERIVATIVES FROM XANTHOHUMOL

The present invention relates to an efficient method for producing naringenin derivatives from xanthohumol or derivatives thereof. In particular, the method according to the present invention provides the production of isoxanthohumol, for example also in enantiomer-enriched form, from xanthohumol and subsequent demethylation of isoxanthohumol according to specific procedures obtaining corresponding naringenin derivatives, such as, in particular, 8-prenylnaringenin.

8-Prenylnaringenin is a potent phytoestrogen (Zierau, O.; Gester, S.; Schwab, P.; Metz, P.; Kolba, S.; Wulf, M.; Vollmer, G. *Planta Med.* 2002, 68, 449-451), which at present is being intensively studied for further biological and pharmacological properties.

Therefore a simple and efficient method for producing corresponding naringenin derivatives, such as, in particular, 8-prenylnaringenin, would be desirable.

Xanthohumol is a yellow solid, the structure of which is derived from the basic framework of chalcone and is one of the flavonoids occurring in natural hops (*Humulus lupulus*). Xanthohumol may be obtained in a simple and economic manner in high yield and high purity from hops (see DE 102 40 065.2). Xanthohumol isomerizes under alkaline conditions to isoxanthohumol. The ether cleavage of isoxanthohumol to form 8-prenylnaringenin, however, creates considerable problems.

Lewis acids, particularly $AlCl_3$, $AlBr_3$, and $BBr_3$, are effective reagents for cleavage of aryl methyl ethers (Greene, Th. W.; Wutz, P. G. M. *Protective Groups in Organic Synthesis* John Wiley & Sons: New York 1999, 250-257). Problems result, in particular, when Lewis-acid-sensitive groups may be found in the starting material. For instance OH groups lead to the formation of acid (for example HX when $AlX_3$ is used) and bind (deactivate) the Lewis acid. Double bonds can react by rearrangement, OH- or HX-addition, Friedel-Crafts or Prins alkylation, undergo cationic rearrangements or in the case of a plurality of double bonds, for example the prenyl series, lead to cyclization products (terpene type cyclization). In the workup, frequently addition of water to the double bond can be observed. The unwanted cleavage of other ethers can also occur, for example cyclic ethers as in flavonoids. Under oxidizing conditions, sometimes just in air, halogenations are also observed.

Although with $BBr_3$ demethylation of an 8-geranyl flavanone succeeded (Wang, Y.; Tan, W.; Li, W. Z.; Li, Y. *J. Nat. Prod.* 2001, 64, 196-199), the application of this method to acid-sensitive derivatives such as, for example, isoxanthohumol principally leads to cyclization products by reaction of the prenyl group with the neighboring OH group and also to the addition of water to the double bond of the prenyl group. With respect to transition metal compounds, to date only for cerium ammonium nitrate is the demethylating action on a 1,4-dimethoxyaromatic to give quinone disclosed (Kawasaki, M.; Matsuda, F.; Terashima, S. *Tetrahedron* 1988, 44, 5713).

To this extent, in the context of the present invention, a novel synthesis method for the demethylation of aryl methyl ethers having acid-labile groups, in particular having vinylic or allylic and hydroxyl groups in the ortho position which cyclize readily under acid catalysis, as can be present in the case of isoxanthohumol and derivatives thereof, is required in order to produce corresponding naringenin derivatives, such as, in particular, 8-prenylnaringenin.

Accordingly, the present invention provides an efficient method for producing naringenin derivatives, such as, in particular, 8-prenylnaringenin, from xanthohumol or derivatives thereof, which comprises the steps:

(1) reaction of xanthohumol or derivatives thereof according to formula (I) hereinafter to give isoxanthohumol or derivatives derived therefrom according to formula (II) hereinafter:

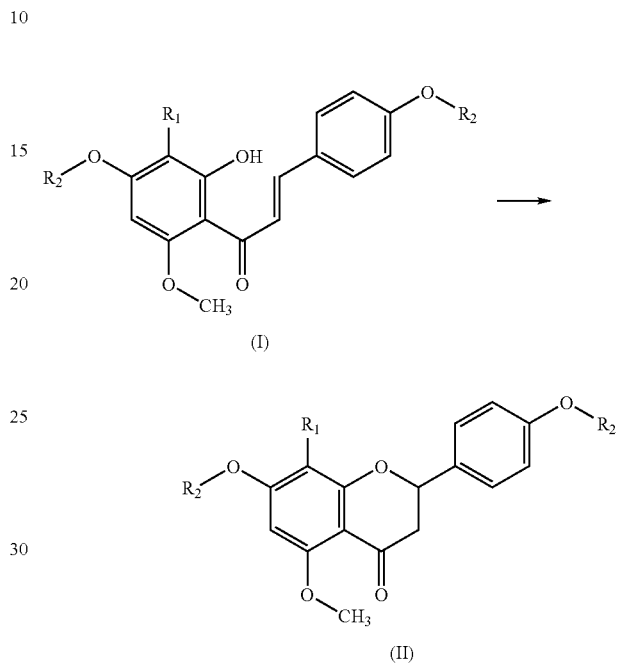

where $R_1$ is an allyl, crotyl, prenyl, geranyl or neryl radical and $R_2$ is selected from the group consisting of hydrogen, a straight-chain or branched-chain ($C_1$-$C_6$)-alkyl radical, a ($C_3$-$C_7$)-cycloalkyl radical, an unsubstituted, monosubstituted or disubstituted phenyl or benzyl radical, where the substituents can be selected from straight-chain or branched-chain ($C_1$-$C_6$)-alkyl radicals and ($C_1$-$C_6$)-alkoxy radicals, a (—C(O)—$R_a$) group, where $R_a$ is selected from hydrogen or straight-chain or branched-chain ($C_1$-$C_6$)-alkyl radicals, and silyl protecting groups, and subsequently (2) demethylation of the compounds according to formula (II), obtaining naringenin derivatives according to formula (III) hereinafter

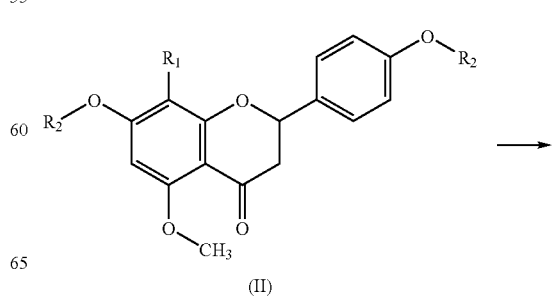

-continued

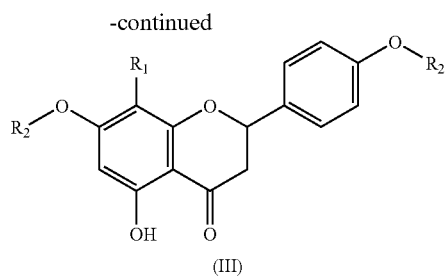

(III)

wherein the demethylation is carried out either
(A) as base-buffered, Lewis acid demethylation, in which a compound according to formula (II) is reacted with a compound of the general formula $MX_3$, where M is a Lewis acid metal ion and X is a halogen, with addition of a base selected from alkali metal alkoxides or tertiary amines, or
(B) as protecting-group-supported, Lewis acid demethylation, in which a compound according to formula (II) in which then the radical $R_2$ independently of one another is a (—C(O)—$R_a$) group, where $R_a$ is selected from hydrogen or straight-chain or branched-chain ($C_1$-$C_6$)-alkyl radicals, or a silyl protecting group, is reacted with a compound of the general formula $MX_3$, where M is a Lewis acid metal ion and X is a halogen, or
(C) as a demethylation such that a compound according to formula (II) is reacted with a compound of the general formula $LY_z$, where L is a lanthanide, scandium or yttrium, Y is Hal, OTs, OTf, OTfa, OMs, $ClO_4$, $BF_4$ or $PHal_6$ and z, depending on the valency of the element L, is an integer from 1 to 4.

Customarily, in the demethylation in the context of steps (A), (B) and (C), as an additive for facilitating the reaction, a nucleophile such as a halide, such as, in particular, iodide, a sulfide such as, for example, an alkyl sulfide, an aryl sulfide or thioacetate, a selenide or a disulfide is added, as is well known to those skilled in the art.

Silyl protecting groups, in the context of the present invention, are taken to mean conventional silylated OH protecting groups, as are specified, for example, in Greene, Th. W.; Wutz P. G. M. *Protective Groups in Organic Synthesis* John Wiley & Sons: New York 1999. Those which can be mentioned here by way of example are those based on $SiHal_3$, $SiAlkyl_3$, $So(OAlkyl)_3$, where Hal is Cl or Br and alkyl, independently of one another, is a straight-chain or branched-chain ($C_1$-$C_6$)-alkyl radical, or mixed substituted silyl protecting groups such as tert-butyldimethylsilyl (TBS) or tert-butydiphenylsilyl, in particular TMS, TES, TIPS and TBS.

Halogen is taken to mean F, Cl, Br and I. Ts is tosylate, Tf is triflate, Tfa is trifluoroacetate and Ms is mesylate.

Surprisingly, after relatively long failed attempts with known methods, three alternative methods (A, B and C) have been found for the demethylation of sensitive aryl methyl ethers such as the isoxanthohumol derivatives used here.

Demethylation method (A) is a base-buffered, Lewis acid demethylation. Customarily, the starting compound according to formula (II) is reacted with 1 to 5 equivalents of a compound of the general formula $MX_3$, where M is preferably boron or a metal of main group 3 and X is a halogen. Particularly preferably, the compounds are $BX_3$ and $AlX_3$, most preferably $BBr_3$ and $AlBr_3$. In addition, 0.5 to 10 equivalents of a base selected from alkali metal alkoxides or tertiary amines, preferably a tertiary amine such as, in particular, collidine, are added to the reaction batch. Preferably, the proportion of base is 1 to 6 equivalents. Both Lewis acid and the base can be bound by ion exchangers or solid phases, also in combination. If appropriate, also auxiliary substances such as a corresponding nucleophile, as already mentioned above, and/or trimethylsilyl chloride can be added to the reaction batch. According to the invention, in the method A, the procedure is performed in a suitable organic solvent customarily below 100° C. Preferably, the reaction is carried out between 0 and 50° C. in a dried inert solvent. Particularly preferably, the reaction is performed at room temperature in dry dichloromethane.

Demethylation method (B) is a protecting-group-supported, Lewis acid demethylation. For protection of the phenolic OH groups of the compounds according to formula (II), the starting compound is reacted with 1 to 5 equivalents (per OH group) of a suitable acyl or silyl compound (cf. also Greene, Th. W.; Wutz, P. G. M. *Protective Groups in Organic Synthesis* John Wiley & Sons: New York 1999). Preferably, per OH group, use is made of 1 to 2 equivalents of TMSCl, TESCl, TIPSCl, TBSCl or acetic anhydride. Particular preference is given to the reaction with 2.5 molar equivalents of chlorotriisopropylsilane. If appropriate, to facilitate the reaction, also a nucleophile, as already mentioned above, can be added, for example iodide, or an additive such as, for example, imidazole. Customarily, then, the protected starting compound according to formula (II) is reacted with 1 to 2 equivalents of a compound of the general formula $MX_3$, where M is preferably boron or a metal of main group 3 and X is a halogen. Particularly preferably, the compounds are $BX_3$ and $AlX_3$, most preferably $BBr_3$ and $AlBr_3$. According to the invention, in the method (B), the procedure is performed in a suitable organic solvent customarily below 100° C. Preferably, the reaction is carried out between 0 and 50° C. in a dried inert solvent. Particular preference is given to the reaction at room temperature in dry dichloromethane. Suitable reactions for eliminating the protecting group in the method (B) are disclosed by Greene, Th. W.; Wutz, P. G. M. *Protective Groups in Organic Synthesis* John Wiley & Sons: New York 1999. Particular preference is given to elimination of the silyl protecting group using HF or tetra-n-butylammonium fluoride in a suitable organic solvent.

In the demethylation method (C) (lanthanide-, scandium- or yttrium-ion-supported demethylation), the starting compound according to formula (II) is reacted in a dried organic solvent with a compound of the general formula $LY_z$, where L is a lanthanide, scandium or yttrium, Y is Hal, OTs, OTf, OTfa, OMs, $ClO_4$, $BF_4$ or $PHal_6$ and z, depending on the valency of the element L, is an integer from 1 to 4. Preferably, the procedure is carried out using an iodide as a further auxiliary substance and a scandium salt. Particular preference is given to the embodiment using potassium iodide and scandium trifluoromethanesulfonate in tetrahydrofuran at approximately 70° C.

In the context of the present invention, in step (1), first xanthohumol is converted into isoxanthohumol. This can proceed in a known manner by isomerization under alkaline conditions. However, in particular, in step (1) isoxanthohumol can be produced in enantiomer-enriched form, by reacting xanthohumol with sparteine under basic conditions (method (I)) or with a chiral phase transfer catalyst such as, for example, the O'Donnell phase transfer catalyst O-allyl-N-(9-anthra-cenylmethyl)cinchonidinium bromide (method (II)), as a result of which, after final HPLC workup, enantiomer-enriched isoxanthohumol or derivatives thereof are obtained. This procedure has the advantage that then in the further demethylation step, enantiomer-enriched naringenin derivatives, such as, for example, (−) or (+)-8-prenylnaringenin, are also obtained. Alternatively, for separation of the racemates or for further enrichment of an enantiomer, use can be made of chiral chromatography columns. However, in this case it is necessary to note that the compounds racemize readily.

In the context of the present invention, $R_1$ is in particular prenyl. The present invention therefore comprises an extremely efficient method for producing 8-prenylnaringenin, for example also in enantiomer-enriched form, starting from xanthohumol, which in turn is obtainable from hop extract.

The invention is described in more detail by the examples hereinafter.

EXAMPLES

All reactions were carried out under argon and in dried solvents. $^1$H- and $^{13}$C-NMR spectra were recorded using a Varian Mercury 300 MHz spectrometer. The chemical shifts are reported in δ values (ppm) using tetramethylsilane as internal standard. ESI-MS spectra were obtained using an API 150 EX spectrometer (Applied Biosystems). Preparative HPLC was carried out on a Merck Hitachi apparatus using a YMC-pack ODS AA12S05-1520WT column at a wavelength of 210 nm using acetonitrile/water. For flash chromatography, use was made of Silicagel 60 (0.040-0.063 nm).
Synthesis of Isoxanthohumol in Racemic Form Xanthohumol (500 mg, 1.4 mmol) is dissolved in 500 ml of 1% NaOH and stirred for 2 h at 0° C. Acidification with 50% $H_2SO_4$ gives a light-yellowish precipitate. After filtration and careful washing with $H_2O$, the dried product is dissolved in methanol and filtered again. After addition of $H_2O$, the methanol is taken off. Lyophilization gives isoxanthohumol in racemic form as light-yellowish powder of >95% purity.

Spectroscopic data: UV: $\lambda_{max}$ 288 nm, $^1$H-NMR: δ 1.60 (s, 3H), 1.61 (s, 3H), 2.62 (dd, 1H, J=16.3, J=2.9 Hz), 2.93 (dd, 1H, J=16.3, J=12.6), 3.26 (d, 1H, J=7.1), 3.73 (s, 3H), 5.20 (t, 1H, J=7.1), 5.36 (dd, 1H, J=12.6, J=2.9), 6.22 (s, 1H), 6.89 (d, 2H, J=8.6), 7.39 (d, 1H, J=8.6); $^{13}$C-NMR: δ 17.87, 22.50, 25.87, 46.12, 55.73, 79.37, 93.49, 106.04, 108.79, 115.85, 123.63, 128.45, 130.83, 131.31, 158.10, 160.84, 161.81, 162.57, 188.49; ESI-MS: 353.3 [M-H]$^-$
Synthesis of Enantiomer-Enriched Isoxanthohumol
Method (I)

To the solution of (−)-sparteine (20 mg, 0.084 mmol) in toluene is added dropwise n-butyllithium (0.052 ml of 1.6M solution in hexane) at −78° C. After 15 min, at −78° C., a solution of xanthohumol (2 OH groups TBMS-protected) (33 mg, 0.056 mmol) is slowly added dropwise. Subsequently, the mixture is allowed to warm to room temperature. After 24 h, the toluene is removed in vacuum, the residue is taken up in petroleum ether/ethyl acetate=5:1 and eluted through a silica gel column using petroleum ether/ethyl acetate.
Method (II)

To the suspension of the O'Donnell phase transfer catalyst O-allyl-N-(9-anthracenylmethyl)cinchonidinium bromide (34 mg, 0.056 mmol) in 1 ml of toluene is added xanthohumol (2 OH groups protected) (in part TIPS-protected: 37 mg, 0.056 mmol) in 1 ml of toluene. Subsequently, 0.5 ml of 25% NaOH is added and the mixture is stirred for 24 h at room temperature. For workup, 20 ml of $H_2O$ and 20 ml of ethyl acetate are added. The aqueous phase is acidified with $H_2SO_4$ and extracted twice with ethyl acetate. The organic phase is washed with $NH_4Cl$ solution and $H_2O$, dried and eluted through a silica gel column using $CHCl_3$/methanol. Removal of protection proceeds in a manner known from the literature.

HPLC Data of the Enantiomers:

Enantiomer separation on Chiralpak AD-H 4.6×250 mm, mobile phase=n-hexane:2-propanol, $R_t$ [min] for the two enantiomers
Isoxanthohumol:
Mobile phase 95:5 $R_t$=107.03 and $R_t$=115.64
TIPS-protected isoxanthohumol:
Mobile phase 98:2 $R_t$=5.34 and $R_t$=6.00
8-Prenylnaringenin:
Mobile phase 90:10 $R_t$=26.31 and $R_t$=41.06

Demethylation According to Method A

1. Reaction of Isoxanthohumol (Formula (II) with $R_1$=prenyl, $R_2$=H) with $AlBr_3$ in the Presence of Collidine To the stirred suspension of isoxanthohumol (50 mg, 0.14 mmol) in 4 ml of $CH_2Cl_2$ is slowly added dropwise sym. collidine (approximately 100 mg, 0.83 mmol) until a yellow solution is formed. At room temperature, 0.28 ml (0.28 mmol) of a 1M solution of $AlBr_3$ in $CH_2Br_2$ is added dropwise and the mixture is stirred overnight. The orange-red precipitate is filtered, washed with $CH_2Cl_2$ and dried in vacuum. Subsequently, the precipitate is dissolved in 10 ml of 0.5M NaOH and stirred for 1.5 h at 0° C. After acidification with 50% $H_2SO_4$, the mixture is filtered and the yellow precipitate is carefully washed with water. After fractionation of the mixture by means of HPLC (40% to 70% acetonitrile in 20 min) and subsequent lyophilization, 12 mg (25%) of 8-prenylnaringenin (formula (III) where $R_1$=prenyl, $R_2$=H) ($R_T$=14.4 min) are produced in addition to 0.5 mg (1%) of xanthohumol ($R_T$=21.1 min) and 27 mg (54%) of starting material ($R_T$=9.6 min). The latter can be recirculated to the reaction.

8-Prenylnaringenin (formula (III) where $R_1$=prenyl, $R_2$=H): UV: $\lambda_{max}$ 293, 335 nm; $^1$H-NMR (acetone-d$_6$): δ 1.60 (s, 3H), 1.61 (s, 3H), 2.76 (dd, 1H, J=17.2 Hz, J=3.1 Hz), 3.14 (dd, 1H, J=17.2 Hz, J=12.8 Hz), 3.22 (d, 2H, J=7.3 Hz), 5.19 (t, 1H, J=7.3), 5.45 (dd, 1H, J=12.8 Hz, J=3.1 Hz), 6.03 (s, 1H), 6.90 (d, 2H, J=8.6), 7.41 (d, 2H, J=8.6), 12.14 (s, 1H); $^{13}$C-NMR (CDCl$_3$): δ 17.93, 21.88, 25.91, 43.17, 78.69, 96.80, 103.11, 106.01, 115.46, 121.42, 127.62, 130.78, 134.96, 155.72, 159.51, 162.03, 163.50, 196.19; ESI-MS: 339.3 [M-H]$^-$ 2. Reaction of Isoxanthohumol (Formula (II) where $R_1$=prenyl, $R_2$=H) with $AlBr_3$ in the Presence of $Me_3SiCl$ and Collidine To the stirred suspension of isoxanthohumol (52 mg, 0.15 mmol) in 5 ml of $CH_2Cl_2$ is slowly added dropwise sym. collidine (approximately 100 mg, 0.83 mmol) until a yellow solution is formed. At room temperature, 35 mg (0.322 mmol) of $Me_3SiCl$ are added. The mixture is stirred for 1 h, subsequently 0.2 ml (0.2 mmol) of a 1M solution of $AlBr_3$ in $CH_2Br_2$ are added dropwise and the mixture is stirred overnight. The solvent is taken off in vacuum and the residue is dissolved in 10 ml of ice-cold 0.5M NaOH. After stirring has been performed for 1.5 h at 0° C., the mixture is acidified with 50% $H_2SO_4$, the yellow precipitate filtered and carefully washed with water. After fractionation of the mixture by means of HPLC (40% to 70% acetonitrile in 20 min) and subsequent lyophilization, 15 mg (30%) of 8-prenylnaringenin (formula (III) where $R_1$=prenyl, $R_2$=H) ($R_T$=14.4 min) in addition to 2.5 mg (5%) of xanthohumol ($R_T$=21.1 min) and 18 mg (35%) of starting material ($R_T$=9.6 min) are obtained, which can again be recirculated to the reaction.

3. Reaction of Isoxanthohumol (Formula (II) where $R_1$=prenyl, $R_2$=H) with $BBr_3$ in the Presence of Collidine To the stirred suspension of isoxanthohumol (51 mg, 0.14 mmol) in 4 ml of $CH_2Cl_2$ is slowly added dropwise sym. collidine (approximately 100 mg, 0.83 mmol) until a yellow solution is formed. At $-80°$ C., 0.5 ml (0.5 mmol) of a 1M solution of $BBr_3$ in $CH_2Cl_2$ is added dropwise and the mixture is stirred for 3 h at $-80°$ C. The solvent is taken off in vacuum and the residue is dissolved in 10 ml of ice-cold 0.5M NaOH and stirred for 1.5 h at $0°$ C. After acidification with 50% $H_2SO_4$, the mixture is filtered and the yellow precipitate is carefully washed with water. After fractionation of the mixture by means of HPLC (40% to 70% acetonitrile in 20 min) and subsequent lyophilization, 9 mg (18%) of 8-prenylnaringenin (formula (III) where $R_1$=prenyl, $R_2$=H) ($R_T$=14.4 min) are obtained in addition to 5 mg (10%) of cyclized 8-prenylnaringenin ($R_T$=20.8 min) and 9 mg (18%) of starting material ($R_T$=9.6 min) which again can be recirculated into the reaction.

Demethylation According to Method B

Synthesis of 7,4"-di-triisopropylsiloxyisoxanthohumol (formula (II) where $R_1$=prenyl, $R_2$=$((CH_3)_2CH_3Si)$)

To the stirred suspension of isoxanthohumol (302 mg, 0.85 mmol) in $CH_2Cl_2$ (10 ml), imidazole (290 mg, 4.26 mmol) is added and subsequently at $0°$ C. chlorotriisopropylsilane (394 mg, 2.04 mmol) is added dropwise. The reaction mixture is allowed to warm slowly to room temperature and stirred overnight. After the solvent has been taken off in vacuum, pentane (10 ml) is added, filtered, and the white precipitate is washed with pentane. The organic solution is washed with (2×10 ml) 5% HCl and (3×10 ml) $H_2O$ and dried over $Na_2SO_4$. The solvent is taken off in vacuum and the residue taken up in a sparing amount of ethyl acetate and eluted by means of flash chromatography through a silica gel column using pentane/ethyl acetate=5:1. 7,4"-di-triisopropylsiloxy-isoxanthohumol is obtained as a light-yellow solid in the second fraction ($R_f$=0.16).

$^1$H-NMR ($CDCl_3$): δ 1.12 (m, 36H), 1.29 (m, 6H), 1.49 (s, 3H), 1.62 (s, 3H), 2.75 (dd, 1H, J=16.5, J=2.9), 2.99 (dd, 2H, J=16.5, J=13.2), 3.26 (d, 2H, J=6.8), 3.84 (s, 3H), 5.12 (t, 1H, J=6.8), 5.28 (dd, 1H, J=13.2, J=2.9), 6.05 (s, 1H), 6.89 (d, 2H, J=8.6), 7.28 (d, 2H, J=8.4); $^{13}$C-NMR ($CDCl_3$): δ 12.74, 13.23, 17.91, 17.99, 18.09, 22.55, 25.86, 45.50, 55.95, 78.62, 95.75, 106.23, 112.53, 119.78, 122.58, 127.43, 130.97, 131.49, 156.02, 159.67, 160.28, 162.04, 190.18; ESI-MS: m/z 667.3 [M$^+$]

Reaction of 7,4"-di-triisopropylsiloxyisoxanthohumol with $AlBr_3$

To the solution of 7,4"-di-triisopropylsiloxyisoxanthohumol (100 mg, 0.15 mmol) in $CH_2Cl_2$ is slowly added dropwise at $0°$ C. a 1M solution of $AlBr_3$ in $CH_2Br_2$ (0.15 ml, 0.15 mmol). After the reaction mixture has been stirred for 30 min at $0°$ C., it is slowly allowed to warm to room temperature and stirred overnight. Subsequently, 10 ml of 0.1M NaOH are added and the mixture is stirred intensively for 15 min. After acidification (50% $H_2SO_4$), the organic phase is separated off using saturated $NH_4Cl$ solution (2×30 ml) and $H_2O$ (1×30 ml) and dried over $Na_2SO_4$. After the solvent has been taken off, the correspondingly silylated 8-prenylnaringenin derivative (formula (III) where $R_1$=prenyl, $R_2$=$((CH_3)_2CH)_3Si)$) is produced as crude product in good purity—no signals for by-products in $^1$H-NMR.

$^1$H-NMR ($CDCl_3$): δ 1.12 (m 36H), 1.29 (m, 6H), 1.50 (s, 3H), 1.62 (s, 3H), 2.76 (dd, 1H, J=17.1, J=3.0), 3.06 (dd, 1H, J=17.1, J=13.1), 3.22 (d, 2H, J=7.0), 5.11 (t, 1H, J=7.0), 5.31 (dd, 1H, J=13.1, J=3.0), 6.00 (s, 1H), 6.91 (d, 2H, J=8.6), 7.28 (d, 2H, J=8.4), 11.97 (s, 1H)

Removal of the Protecting Group

1. Using Tetra-N-Butylammonium Fluoride

To a solution of the correspondingly silylated 8-prenylnaringenin derivative (formula (III) where $R_1$=prenyl, $R_2$=$((CH_3)_2CH)_3Si)$) (98 mg, 0.15 mmol) in THF (3 ml) is added slowly dropwise at $0°$ C. a 1M solution of tetra-n-butylammonium fluoride in THF (0.36 ml, 0.36 mmol). The reaction mixture is allowed to warm to room temperature and is stirred for a further 1 h. After addition of toluene (5 ml), the solvent is taken off in vacuum, the residue dissolved in a sparing amount of $CHCl_3$ and eluted through a silica gel column using $CHCl_3$/methanol=100:1 for removing the n-$Bu_4N^+$ and polymeric silicon compounds. 8-Prenylnaringenin (formula (III) where $R_1$=prenyl, $R_2$=H) (43 mg, 84%) is obtained as yellowish solid.

2. Using Pyridine.HF

To a solution of the correspondingly silylated 8-prenylnaringenin derivative (formula (III) where $R_1$=prenyl, $R_2$=$((CH_3)_2CH)_3Si)$) (95 mg, 0.15 mmol) in THF (5 ml), pyridine-HF (0.3 ml) is added and the mixture is stirred for 3 days at room temperature. The reaction mixture is admixed with 5 ml of saturated $MgCl_2$ solution and 1M NaOH until the pH is approximately 3. Subsequently, the mixture is extracted by shaking with $CH_2Cl_2$ (2×30 ml) and the combined organic phases are washed with saturated $NH_4Cl$ solution (2×30 ml) and $H_2O$ (1×30 ml). The organic phase is concentrated and eluted through a silica gel column using $CHCl_3$/methanol=100:1. 8-Prenylnaringenin (formula III) where $R_1$=prenyl, $R_2$=H) is obtained (25 mg, 50%) as a yellowish solid.

Demethylation According to Method C

Reaction of Isoxanthohumol (Formula (II) where $R_1$=Prenyl, $R_2$=H) with Scandium Trifluoromethane-Sulfonate To a mixture of isoxanthohumol (50 mg, 0.14 mmol), KI (34 mg, 0.21 mmol) and Sc(OTf)$_3$ (105 mg, 0.21 mmol), 10 ml of THF are added and the solution is heated for 2.5 h under reflux. The mixture is stirred overnight at room temperature and concentrated in vacuum. The scandium salt is separated off via a short silica gel column (eluted with $CHCl_3$/methanol=100:1). The resultant solution is concentrated to dryness in vacuum, the residue is taken up in $CHCl_3$ and eluted through a silica gel column using $CHCl_3$/-methanol=100:1. 8-Prenylnaringenin (formula (III) where $R_1$=prenyl, $R_2$=H) (44 mg, 92%) is obtained as a light-yellowish solid.

The invention claimed is:

1. A method for producing naringenin derivatives from xanthohumol or derivatives thereof, which comprises the steps:

(1) reaction of xanthohumol or derivatives thereof according to formula (I) hereinafter to give isoxanthohumol or derivatives derived therefrom according to formula (II) hereinafter:

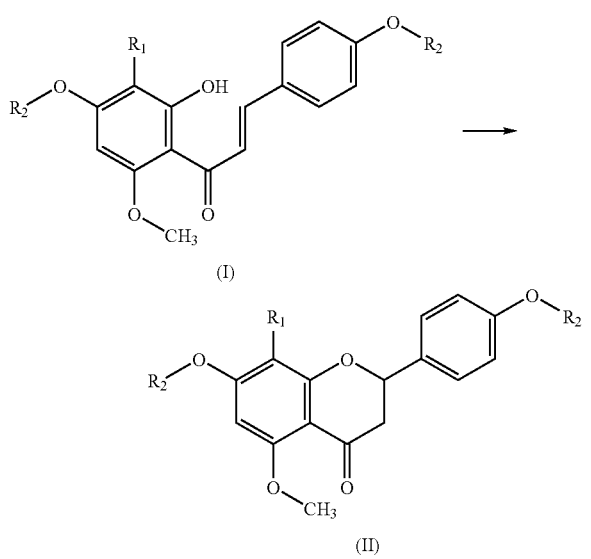

(I)

(II)

where
R₁ is an allyl, crotyl, prenyl, geranyl or neryl radical and
R₂ is selected from the group consisting of hydrogen, a straight-chain or branched-chain ($C_1$-$C_6$)-alkyl radical, a ($C_3$-$C_7$)-cycloalkyl radical, an unsubstituted, mono-substituted or disubstituted phenyl or benzyl radical, where the substituents can be selected from straight-chain or branched-chain ($C_1$-$C_6$)-alkyl radicals and ($C_1$-$C_6$)-alkoxy radicals, a (—C(O)—$R_a$) group, where $R_a$ is selected from hydrogen or straight-chain or branched-chain ($C_1$-$C_6$)-alkyl radicals, and silyl protecting groups, and subsequently (2) demethylation of the compounds according to formula (II), obtaining naringenin derivatives according to formula (III) hereinafter

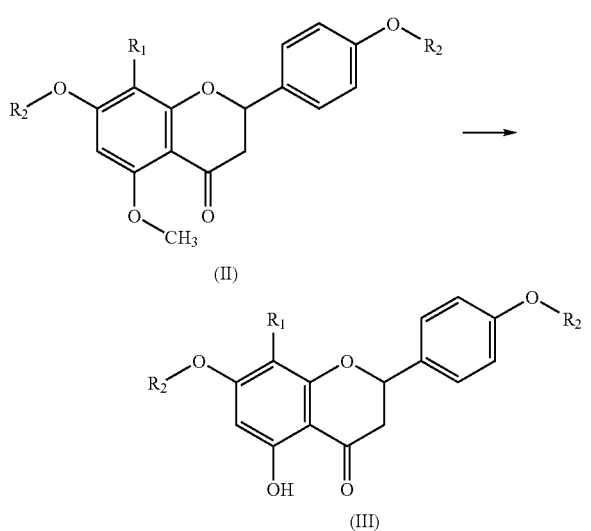

(II)

(III)

wherein the demethylation is carried out either (A) as base-buffered, Lewis acid demethylation, in which a compound according to formula (II) is reacted with a compound of the general formula $MX_3$, where M is a Lewis acid metal ion and X is a halogen, with addition of a base selected from alkali metal alkoxides or tertiary amines, or (B) as protecting-group-supported, Lewis acid demethylation, in which a compound according to formula (II) in which then the radical $R_2$ independently of one another is a (—C(O)—$R_a$) group, where $R_a$ is selected from hydrogen or straight-chain or branched-chain ($C_1$-$C_6$)-alkyl radicals, or a silyl protecting group, is reacted with a compound of the general formula $MX_3$, where M is a Lewis acid metal ion and X is a halogen, or (C) as a demethylation such that a compound according to formula (II) is reacted with a compound of the general formula $LY_z$, where L is a lanthanide, scandium or yttrium, Y is Hal, OTs, OTf, OTfa, OMs, $ClO_4$, $BF_4$ or $PHal_6$ and z, depending on the valency of the element L, is an integer from 1 to 4.

2. The method as claimed in claim 1, wherein, in step (1), first xanthohumol is converted by isomerization under alkaline conditions into isoxanthohumol.

3. The method as claimed in claim 1, wherein, in step (1), xanthohumol or a derivative thereof is reacted with sparteine under basic conditions or with a chiral phase transfer catalyst, as a result of which, after final HPLC workup, enantiomerically pure isoxanthohumol or a derivative thereof is obtained.

4. The method as claimed in claim 3, wherein, as the chiral phase transfer catalyst, O-allyl-N-(9-anthracenylmethyl)cinchonidinium bromide is selected.

5. The method as claimed in claim 1, wherein, in the demethylation method (A), the compound of the general formula $MX_3$ is $BBr_3$ or $AlBr_3$, and collidine is used as base.

6. The method as claimed in claim 1, wherein, in the demethylation method (B), the starting compound according to formula (II) is reacted with, per OH group, 1 to 2 equivalents of TMSCl, TESCl, TIPSCl, TBSCl or acetic anhydride and then the protected starting compound is reacted with 1 to 2 equivalents of $BBr_3$ or $AlBr_3$.

7. The method as claimed in claim 1, wherein, in the demethylation method (C), the starting compound according to formula (II) is reacted with a scandium salt.

8. The method as claimed in claim 7, wherein the scandium salt is scandium trifluoromethanesulfonate.

9. The method as claimed in claim 1, wherein $R_1$ is prenyl.

10. The method as claimed in claim 1, wherein the naringenin derivative is 8-prenylnaringenin.

* * * * *